United States Patent [19]

Berkowitz

[11] 4,273,928
[45] Jun. 16, 1981

[54] PREPARATION OF SALTS OF DIHALOGENATED ISOCYANURATES BY OXIDATIVE HYDROLYSIS OF AMINO SUBSTITUTED TRIAZINES

[75] Inventor: Sidney Berkowitz, Highland Park, N.J.

[73] Assignee: FMC Corporation, Philadelphia, Pa.

[21] Appl. No.: 721,297

[22] Filed: Sep. 8, 1976

[51] Int. Cl.³ .................. C07D 251/26; C07D 251/32; C07D 251/34; C07D 251/36
[52] U.S. Cl. .................................................. 544/190
[58] Field of Search ..................... 260/248 C; 544/190

[56] References Cited

U.S. PATENT DOCUMENTS

| 2,956,056 | 10/1960 | Christian | 260/248 |
|---|---|---|---|
| 3,896,213 | 7/1975 | Mirdler | 260/248 |
| 4,007,182 | 2/1977 | Wojtowicz | 260/248 |
| 4,024,140 | 5/1977 | Wojtowicz | 260/248 |

Primary Examiner—John M. Ford

[57] ABSTRACT

Salts of dihalogenated isocyanurates are prepared by reacting amino substituted triazines with at least stoichiometric amounts of a halogen containing compound at a temperature of 35° to 70° C. and at a pH value of 6.5 to 11.0 until all of the available sites on the triazine molecule are N-halogenated and N, N-dihalogenated exocyclic nitrogen is removed.

21 Claims, No Drawings

PREPARATION OF SALTS OF DIHALOGENATED ISOCYANURATES BY OXIDATIVE HYDROLYSIS OF AMINO SUBSTITUTED TRIAZINES

This invention relates to the formation of salts of dihalogenated isocyanurates, namely salts of dichlorinated or dibrominated isocyanurates by reacting an amino substituted triazine with a halogen containing compound consisting essentially of sodium hypochlorite, lithium hypochlorite, potassium hypochlorite, sodium hypobromite, potassium hypobromite, lithium hypobromite, and calcium hypochlorite in an aqueous medium.

Cyanuric acid is commonly represented as existing in two tautomeric forms as follows:

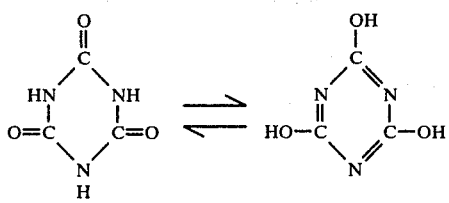

The terms dichloroisocyanuric acid and dichloroisocyanurate refer to the acid and salt respectively in either tautomeric form.

Cyanuric acid is the main product produced by heating urea, biuret or mixtures thereof in a kiln at temperatures of about 200° to 350° C. Unfortunately, the product produced is only composed of about 80% cyanuric acid with the remainder of the product comprising amino substituted triazine impurities. The amino substituted triazine impurities generally contain about 25% ammelide and minor amounts of other impurities such as ammeline, melamine, ammeline:ammelide complex, and cyanuric acid:melamine complex. This cyanuric acid product mixture is conventionally referred to as crude cyanuric acid. Since it is quite difficult to separate the crude cyanuric acid into its component parts to recover pure cyanuric acid, various methods have been proposed to purify crude cyanuric acid by converting the triazine impurities into cyanuric acid by acid hydrolysis. This conversion is sometimes referred to as the acid digestion process.

The acid digestion process comprises mixing crude cyanuric acid with a strong mineral acid to make a slurry containing 10% to 15% undissolved solids. The mineral acids disclosed as being operative are sulfuric, hydrochloric, nitric and phosphoric acid, with sulfuric acid being preferred. The slurry is digested at reflux temperatures (about 104° C.) or at higher temperatures while under pressure. These digestion processes result in hydrolysis of most of the triazine impurities to cyanuric acid. Methods employing this procedure are described in U.S. Pat. Nos. 2,768,167, 2,943,088 and 3,107,244.

The use of mineral acid reactions, however, results in partial hydrolysis of the cyanuric acid to ammonia and carbon dioxide, thus decreasing cyanuric acid yields. The formation of a purified cyanuric acid, however, is essential for efficient conversion of the cyanuric acid into chloroisocyanuric acids and their salts, preferably sodium, lithium or potassium salts, by known processes employed in the prior art.

Dichloroisocyanuric acid and trichloroisocyanuric acid have been produced by mixing purified cyanuric acid with sodium hydroxide and then chlorinating by the addition of chlorine. Specifically, dichloroisocyanuric acid has been produced by mixing cyanuric acid and sodium hydroxide in a mole ratio of 1:2 and then chlorinating the mixture by the addition of chlorine, usually in two stages, until the pH value is between 1.7 and 3.5. This process requires long hold-up times for the chlorination reaction to approach completion and therefore the reactors must be relatively large to obtain sufficient hold-up times and yields.

U.S. Pat. No. 3,035,056 discloses a process for producing sodium dichloroisocyanurate dihydrate by chlorinating 1 mole of trisodium cyanurate with 2 moles of trichloroisocyanuric acid. Such a reaction is disadvantageous since it requires a separate source of trichloroisocyanuric acid to obtain the required reactant for the process.

U.S. Pat. No. 3,712,891 discloses another process for producing chloroisocyanuric acids by reacting purified cyanuric acid and hypochlorous acid in an aqueous medium at a temperature of 0° to 50° C. The molar ratio of cyanuric acid to hypochlorous acid is preselected to yield a product having the desired degree of chlorination, that is, a molar ratio of cyanuric acid to hypochlorous acid of 1:2 produces dichloroisocyanuric acid, whereas a molar ratio of cyanuric acid and hypochlorous acid of 1:3 produces trichloroisocyanuric acid.

It has been unexpectedly discovered that salts of dihalogenated isocyanurates can be produced directly from amino substituted triazines without the need for any preliminary purification means, by reacting an amino substituted triazine with at least stoichiometric amounts of a halogen containing compound selected from the group consisting of sodium hypochlorite, lithium hypochlorite, potassium hypochlorite, sodium hypobromite, lithium hypobromite, potassium hypobromite, and calcium hypochlorite, in an aqueous medium at a temperature of 35° to 70° C. and at a pH value of 6.5 to 11.0 for less than about five minutes to completely N-halogenate all of the available sites on the triazine molecule that can be N-halogenated and to remove any N, N-dihalogenated exocyclic nitrogens; cooling the reaction medium to precipitate a salt of a dihalogenated isocyanurate; and recovering the salt of a dihalogenated isocyanurate.

The process of the invention permits the formation of salts of dihalogenated isocyanurates, namely salts of dichlorinated or dibrominated isocyanurates, directly from amino substituted triazines in a commercially simple and efficient manner. The conversion is performed without the concomitant metal corrosion problems associated with the prior art acid digestion processes, without the need for large expensive acid digestor reactors, and without the long hold-up times required for the prior art chlorination reactions to approach completion. It also permits the recovery of salts of dihalogenated isocyanurates in exceptionally high yields and exceptionally high purities in relatively short periods of time, that is below about five minutes.

In the process of the invention, an amino substituted triazine, such as melamine, ammeline, ammelide, ammeline: ammelide complex and cyanuric acid:melamine complex, are mixed with a sufficient amount of a halogen containing compound to completely N-halogenate all of the available sites on the triazine molecule that can be N-halogenated and to remove any N, N-dihalogenated exocyclic nitrogens. Alternatively, crude cyanuric acid containing ammelide and other amino substituted triazine impurities is mixed with the halogen containing compound and treated according to the process of the invention to likewise completely N-halogenate all of the available sites on the triazine molecule that can be N-halogenated and to remove any N, N-dihalogenated exocyclic nitrogens. The phrase "amino substituted triazines" as used herein, refers to the specific amino substituted triazines enunciated above as well as to crude cyanuric acid.

The amino substituted triazines are employed in amounts sufficient to produce an amino substituted triazine slurry in the aqueous reaction solution. The amino substituted triazine slurry concentration is not critical. However, from a commercial process standpoint, slurry concentrations from 2 to 20 weight % of the amino substituted triazine based on the weight of the reaction solution are desirable. Slurry concentrations below about 2 weight % are not economical in view of the small amounts of material being treated. Slurry concentrations above about 20 weight % are difficult to handle and accordingly are not advisable. Preferably, the slurry concentration is between 6 and 14 weight % based upon the weight of the reaction solution.

The amino substituted triazine slurry is obtained by either mixing dry amino substituted triazine and the halogen containing compound in water or mixing aqueous solutions of one or both of these materials together.

The halogen containing compounds employed in this invention are selected from the group consisting of sodium hypochlorite, lithium hypochlorite, potassium hypochlorite, sodium hypobromite, lithium hypobromite, potassium hypobromite, calcium hypochlorite and hypochlorous acids. These compounds may be employed either singly or in combination.

To achieve complete conversion of the amino substituted triazine to the salt of a dihalogenated isocyanurate, at least stoichiometric amounts of the halogen containing compound must be employed to completely N-halogenate all of the available sites on the triazine molecule that can be N-halogenated and to remove any N, N-dihalogenated exocyclic nitrogens. These amounts will vary with the particular amino substituted triazine, as well as with the starting material and desired halogenated triazine product.

Salts of dichloroisocyanurates are produced when the mole ratio of halogen containing compound to melamine is 11:1, the ratio of halogen containing compound to ammeline is 8:1, or the ratio of halogen containing compound to ammelide is 5:1. The mole ratio of halogen containing compound to amino substituted triazine complexes or to crude cyanuric acid is determined from the aforementioned stoichiometry based upon the specific amino substituted triazine which is present.

Any stoichiometry less than that stated results in the undesirable production of a mixture containing halogenated amino substituted triazines and halogenated isocyanuric acids or their salts, which mixture requires extensive purification procedures to prepare substantially pure salts of dihalogenated isocyanurates.

The stoichiometric reaction results in the formation of 1 mole of nitrogen trichloride for each exocyclic amino group removed from the triazine molecule. The nitrogen trichloride formed during the reaction may be removed by conventional procedures, such as by sparging the reaction medium with an inert gas and removing the sparged nitrogen trichloride as a waste stream. Other well known procedures for removing nitrogen trichloride from a reaction medium may likewise be employed, which procedures do not consititute a part of this invention.

The explosive conditions created by the production of nitrogen trichloride may be minimized by carrying out the reaction at a pH value of 6.5 to 10.0 in the presence of excess amounts of the halogen containing compound. Preferably, the halogen containing compound is employed in amounts of 2% to 30% above the stoichiometric amount necessary to completely N-halogenate all of the available sites on the triazine molecule that can be N-halogenated and to remove any N, N-dihalogenated exocyclic nitrogens. For example, when sodium hypochlorite is used as the halogen containing compound at these higher pH values a large portion of the nitrogen trichloride generated is rapidly converted by hydrolysis to monochloroamine, sodium chloride and nitrogen according to the following theoretical chemical reactions:

$$NCl_3 + 2NaOH \rightleftharpoons NH_2Cl + 2NaOCl$$

$$NH_2Cl + NaOH \rightleftharpoons NaOCl + NH_3$$

$$2NH_3 + 3NaOCl \rightleftharpoons 3NaCl + N_2 + 3H_2O$$

These reaction conditions are only effective for producing the alkaline metal salts of the halogenated isocyanuric acids.

Conversion of the amino substituted triazines into salts of dihalogenated isocyanurates is effected at pH values from 6.5 to 11.0 and at temperatures from 35° C. to 70° C. Higher temperatures should not be employed since these increase triazine ring rupture, thus decreasing product yield. Maximum conversion of the amino substituted triazines into salts of chlorinated isocyanuric acid is achieved at pH values of 6.5 to 10.0 and at temperatures of 35° to 70° C. and preferably at pH values maintained between 7.5 and 9.0 and at temperatures maintained between 35° and 55° C. Maximum conversion of the amino substituted triazines into salts of brominated isocyanuric acids is achieved at pH values of 10.0 to 11.0 and at temperatures of 35° to 70° C. and preferably at temperatures maintained between 55° and 70° C.

Reaction between the amino substituted triazine and the halogen containing compound is extremely rapid under operating conditions with complete conversions being achieved in a matter of minutes. There is, however, a competing reaction causing triazine ring breakdown, which reaction occurs at a slightly slower rate. In order to maximize conversion of the amino substituted triazines into salts of dihalogenated isocyanurates while minimizing triazine ring rupture, the reaction is carred out in less than about 5 minutes and preferably in less than about 2 minutes. These reaction times can be achieved by employing conventional reactors. Reaction times of up to 90 seconds are feasible with commercially available pipe reactors. A pipe reactor is an elongated tubular reaction chamber wherein the feed enters the reactor in one end and product exits out the other end. The reaction takes place within the tube which is heated by external sources. Use of pipe reactors greatly increases the production of the salts of dihalogenated isocyanurates of this invention and eliminates the need for larger type reactors.

Mixing of the amino substituted triazine and halogen containing compound to form the resulting slurry as well as heating the aqueous medium are achieved by conventional means and procedures. Mixing and heating may be done separately or carried out in a single stage. Since this is an exothermic reaction, temperature control of the aqueous reaction medium is easily achieved by conventional external cooling means. The reaction is then permitted to go to completion. Since the reaction proceeds from a dark orange color to a pale yellow color at completion, the reaction may be monitored colorimetrically.

When the reaction is complete, the aqueous solution containing the salts of dihalogenated isocyanurates is cooled by conventional means to precipitate the salt crystals. Preferably, the reaction solution is rapidly cooled in less than about 10 minutes to below about 20° C. and preferably to below about 10° C. Cooling is essential to prevent triazine losses due by ring rupture and to lower the solubility of the salts of dihalogenated isocyanurates in the reaction medium. The precipitated crystals are recovered from the reaction mixture by any conventional liquid-solid separatory means.

The recovered crystals may then be optionally dryed and stored. Drying may be carried out in any conventional manner to remove residual moisture and to produce a free-flowing crystalline product. These procedures are well known in the art and do not constitute a part of the invention.

The invention will be better understood from a consideration of the following examples. The examples are given to illustrate the invention, and are not deemed to be limiting thereof. All percentages given are based on weight unless otherwise indicated.

EXAMPLE 1 Run 1

Production of Sodium Dichloroisocyanurate Dihydrate

A 7.65 gram (0.0593 mole) sample of crude cyanuric acid prepared from urea assaying 78.8% cyanuric acid, 17.65% ammelide, 3.35% ammeline and 0.19% melamine was added to 86.4 grams of an aqueous solution containing 15.45 grams sodium hypochlorite. This addition took place in less than two seconds. The aqueous solution had a pH value of 8.6 and a temperature of 26° C. Almost immediately upon addition, the reaction solution became deep orange in color changing to pale yellow after 90 seconds. Upon addition of crude cyanuric acid, the reaction temperature rose to 40° C. and was maintained at 40° C. for two minutes. The reaction vessel was then quenched in an ice bath and the reaction solution rapidly cooled to 10° C. within two minutes. The reaction vessel was removed from the ice bath, and the crystallized precipitate was filtered from the slurry, washed and air dried at 40° C. to remove surface water. The precipitate was identified as pure sodium dichloroisocyanurate dihydrate. The total yield was 13.73 grams which is equivalent to 90.6% recovery based on starting triazines.

EXAMPLE 2

Runs 2 to 5, and Comparative Run A

The procedure of Example 1 was repeated except that ammelide, ammeline, and melamine were used in place of crude cyanuric acid. The process conditions and results are set forth in Table I.

The phrase "NaOCl/Amino-Triazine Ratio" represents the mole ratio of sodium hypochlorite to amino substituted triazine in the reaction solution. The phase "% Aminotriazine Hydrolyzed" represents the percentage of amino substituted triazines converted to chlorinated isocyanurates. The phrase "% triazine recovered" represents the amount of chlorinated isocyanurates recovered expressed as percent triazines based on 100% starting triazines.

Runs 2 to 5 demonstrate that complete conversion of the amino substituted triazines is achieved by employing stoichiometric amounts of sodium hypochlorite. When less than stoichiometric amounts are employed, the degree of hydrolysis is drastically altered as demonstrated in Comparative Run A.

EXAMPLE 3

Runs 6 to 10, and Comparative Runs B to F

The procedure of Example 1 was repeated except that the reaction pH value and sodium hypochlorite to amino substituted triazine mole ratios were varied as set forth in Table II. For each pH value there were two runs, one in which the mole ratio of sodium hypochlorite to amino substituted triazine was slightly less than theoretical and the other run at proper stoichiometry in which there is an excess of sodium hypochlorite. In all cases, the experiments with the low mole ratios had lower degrees of hydrolysis and lower overall triazine balances. As evidenced by Runs 9 and 10, triazine instability tended to increase at pH levels above 9.0. The reaction products of the Comparative Runs contained mixtures of chlorinated amino-triazines and chlorinated isocyanurates. The phrase "NaOCl/triazine Ratio" represents the mole ratio of sodium hypochlorite to the total triazine content of the solution assaying 78.8% cyanuric acid, 17.65% ammelide, 3.35% ammeline and 0.19% melamine.

EXAMPLE 4

Runs 11 to 16

This example demonstrates the use of alkali metal and alkaline earth metal hypochlorites to prepare various halogenated isocyanurates.

The procedure of Example 1 was repeated except that various halogen containing compounds were employed for sodium hypochlorite. The amino substituted triazine employed and process conditions employed are set forth in Table III with the results.

The invention being thus described, it will be obvious that the same may be varied in many ways. Such variations are not to be regarded as a departure from the spirit and scope of the invention, and all such modifications are intended to be included within the scope of the following claims.

TABLE I

| Run # | Amino Substituted Triazine | Slurry Conc (%) | Reaction pH | Reaction Temp (°C.) | Reaction Time (Min) | NaOCl/ Amino- Triazine Ratio | % Aminotriazine Hydrolyzed | % Triazine Recovered |
|---|---|---|---|---|---|---|---|---|
| 2 | Ammelide | 5 | 6.6 | 50-55 | 2 | 5/1 | 100 | 85 |

TABLE I-continued

| Run # | Amino Substituted Triazine | Slurry Conc (%) | Reaction pH | Reaction Temp (°C.) | Reaction Time (Min) | NaOCl/ Amino-Triazine Ratio | % Aminotriazine Hydrolyzed | % Triazine Recovered |
|---|---|---|---|---|---|---|---|---|
| 3 | Ammelide | 5 | 6.5 | 50–55 | 2 | 5/1 | 100 | 84 |
| 4 | Ammeline | 3 | 6.5 | 55–60 | 2 | 8/1 | 100 | 71 |
| 5 | Melamine | 2.3 | 6.5 | 55–60 | 2 | 11/1 | 100 | 72.5 |
| Comp. Run A | Ammelide | 5 | 6.5 | 50–55 | 2 | 3/1 | 44.0 | 78.0 |

TABLE II

| Run # | Slurry Conc % | Rx pH | Rx Temp °C. | NaOCl/ Triazine Ratio | % Aminotriazine Hydrolyzed | % Triazine Recovered |
|---|---|---|---|---|---|---|
| Comparative Run B | 7.3 | 7.4 | 45 | 2.48/1 | 64.8 | 94.5 |
| Run 6 | 7.3 | 7.4 | 45 | 3.34/1 | 87.7 | 87.1 |
| Comparative Run C | 8.0 | 8.2 | 45 | 2.48/1 | 70.0 | 75.9 |
| Run 7 | 8.0 | 8.2 | 45 | 3.34/1 | 100 | 88.9 |
| Comparative Run D | 8.0 | 8.6 | 45 | 2.48/1 | 90.2 | 71.8 |
| Run 8 | 8.0 | 8.6 | 45 | 3.34/1 | 100 | 90.2 |
| Comparative Run E | 8.0 | 9.0 | 45 | 2.48/1 | 90.0 | 75.0 |
| Run 9 | 8.0 | 9.0 | 45 | 3.34/1 | 100 | 82.4 |
| Comparative Run F | 8.0 | 9.8 | 45 | 2.48/1 | 78.4 | 70.8 |
| Run 10 | 8.0 | 9.8 | 43 | 3.34/1 | 100 | 75.8 |

TABLE III

| Run # | Starting Feed | Halogen Containing Compound Employed | Slurry Conc % | Rx pH | Rx Temp °C. | Rx Time (Min) | Reactant Mole Ratio | % Amino Triazine Hydrolyzed | % Triazine Recovered | Product |
|---|---|---|---|---|---|---|---|---|---|---|
| 11 | CCA* | LiOCl | 7.6 | 8.6 | 45–50 | 1.5 | 3.34/1 | 100 | 85.5 | Lithium dichloroisocyanurate |
| 12 | Ammelide | LiOCl | 5.0 | 8.6 | 50–55 | 1.5 | 5.0/1 | 100 | 79.1 | Lithium dichloroisocyanurate |
| 13 | Ammelide | LiOCl | 5.0 | 8.6 | 50–55 | 2.5 | 5.0/1 | 100 | 74.0 | Lithium dichloroisocyanurate |
| 14 | CCA | Ca(OCl)$_2$ | 8.2 | 8.6 | 45–50 | 2.0 | 3.34/1 | 100 | 87.0 | Calcium di(dichloroisocyanurate) |
| 15 | Ammelide | NaOBr | 3.0 | 10.6 | 60–65 | 5.0 | 5.5/1 | 97.0 | 75.0 | Sodium dibromoisocyanurate |
| 16 | CCA | KOCl | 7.0 | 8.5 | 55 | 1.0 | 3.34/1 | 100 | 86.8 | Potassium dichloroisocyanurate |

*Crude Cyanuric Acid

What is claimed is:

1. A process for preparing a salt of dihalogenated isocyanurate from an amino substituted triazine selected from the group consisting of melamine, ammeline, ammelide, ammeline:ammelide complex, cyanuric acid:-malamine complex, and crude cyanuric acid, which comprises:
   reacting the amino substituted triazine with at least stoichiometric amounts of a halogen containing compound selected from the group consisting of sodium hypochlorite, lithium hypochlorite, potassium hypochlorite, sodium hypobromite, lithium hypobromite, potassium hypobromite, and calcium hypochlorite in an aqueous medium at a temperature of 35° to 70° C., and at a pH value of 6.5 to 11.0 for less than about five minutes to completely N-halogenate all of the available sites on the triazine molecule that can be N-halogenated and to remove any N, N-dihalogenated exocyclic nitrogens;
   cooling the reaction medium to precipitate a salt of a dihalogenated isocyanurate; and
   recovering the salt of a dihalogenated isocyanurate.

2. The process of claim 1 wherein the aqueous medium contains 2 to 20 weight % of the amino substituted triazine based on the weight of the reaction solution.

3. The process of claim 1 wherein the reaction medium is maintained at a temperature between 35° and 55° C., and at a temperature between 35° and 55° C., and at a pH value between 7.5 and 9.0 for less than about two minutes.

4. The process of claim 1 wherein the reaction medium is maintained at a temperature between 55° and 70° C., and at a pH value of 10.0 to 11.0 for less than about two minutes.

5. The process of claim 1 wherein sodium hypochlorite is reacted with said amino substituted triazine to produce sodium dichloroisocyanurate dihydrate.

6. The process of claim 1 wherein potassium hypochlorite is reacted with said amino substituted triazine to produce potassium dichloroisocyanurate.

7. The process of claim 1 wherein lithium hypochlorite is reacted with said amino substituted triazine to produce lithium dichloroisocyanurate.

8. The process of claim 1 wherein sodium hypobromite is reacted with said amino substituted triazine to produce sodium dibromoisocyanurate.

9. The process of claim 1 wherein potassium hypobromite is reacted with said amino substituted triazine to produce potassium dibromoisocyanurate.

10. The process of claim 1 wherein lithium hypobromite is reacted with said amino substituted triazine to produce lithium dibromoisocyanurate.

11. The process of claim 1 wherein calcium hypochlorite is reacted with said amino substituted triazine to produce calcium di(dichloroisocyanurate).

12. The process of claim 1 wherein the reaction solution is rapidly cooled to below about 20° C. to precipitate the salt of a dihalogenated isocyanurate.

13. A process for preparing an alkali metal dichloroisocyanurate from an amino substituted triazine selected from the group consisting of melamine, ammeline, ammelide, ammeline:ammelide complex, cyanuric acid:melamine complex and crude cyanuric acid, which comprises:

reacting in an aqueous medium the amino substituted triazine with an alkali hypochlorite selected from the group consisting of sodium hypochlorite, potassium hypochlorite and lithium hypochlorite at a temperature of 35° to 70° C., and at a pH value of 6.5 to 10.0 for less than about five minutes, said alkali metal hypochlorite being employed in amounts of 2% to 30% above the stoichiometric amounts necessary to completely N-chlorinate all of the available sites on the triazine molecule that can be N-chlorinated and to remove any N, N-dichloro exocyclic nitrogens:

cooling the reaction medium to precipitate alkali metal dichloroisocyanurate; and recovering the alkali dichloroisocyanurate.

14. The process of claim 13 wherein the aqueous medium contains 2 to 20 weight % of the amino substituted triazine based on the weight of the reaction solution.

15. The process of claim 13 wherein the reaction temperature is maintained between 35° and 55° C.

16. The process of claim 13 wherein the reaction pH value is maintained between 7.5 and 9.0.

17. The process of claim 13 wherein the reaction is carried out in less than about two minutes.

18. The process of claim 13 wherein the reaction solution is rapidly cooled to below about 20° C. to precipitate the alkali metal dichloroisocyanurate.

19. The process of claim 13 wherein said alkali metal hypochlorite is reacted with melamine, and the alkali metal hypochlorite is employed in amounts of 2% to 30% above a mole ratio of alkali metal hypochlorite to melamine of 11:1.

20. The process of claim 13 wherein said alkali metal hypochlorite is reacted with ammeline and the alkali metal hypochlorite is employed in amounts of 2% to 30% above a mole ratio of alkali metal hypochlorite to ammeline of 8:1.

21. The process of claim 13 wherein said alkali metal hypochlorite is reacted with ammelide, and the alkali metal hypochlorite is employed in amounts of 2% to 30% above a mole ratio of alkali metal hypochlorite to ammelide of 5:1.

* * * * *